(12) United States Patent
Paldus et al.

(10) Patent No.: US 6,466,322 B1
(45) Date of Patent: Oct. 15, 2002

(54) SWEPT CONTINUOUS WAVE CAVITY RING-DOWN SPECTROSCOPY

(75) Inventors: Barbara A. Paldus, Mountain View; Richard N. Zare, Stanford, both of CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/470,903

(22) Filed: Dec. 23, 1999

Related U.S. Application Data
(60) Provisional application No. 60/114,441, filed on Dec. 31, 1998.

(51) Int. Cl.⁷ .............................................. G01N 21/61
(52) U.S. Cl. ..................................................... 356/437
(58) Field of Search .................................. 356/432, 436, 356/437, 438, 439, 440

(56) References Cited

U.S. PATENT DOCUMENTS

| | | | |
|---|---|---|---|
| 4,571,085 A | 2/1986 | Anderson | 356/445 |
| 6,084,682 A | * 7/2000 | Zare et al. | 356/437 |

OTHER PUBLICATIONS

Levenson, Optical heterodyne detection in cavity ringdown spectroscopy, Chem. Phys. Let., 290, pp. 335, 1998.
Rempe, Measurement of ultralow losses in an optical interferometer, Opt. Let., 17(5), pp. 363, 1992.
Romanini, CW cavity ring down spectroscopy, Chem. Phys. Let., 264, pp. 316, 1997.
Anderson, Mirror reflectometer based on optical cavity decay time, Appl. Phys., 23(8), pp. 1238, 1984.
Engeln, Phase shift cavity ring down absorption spectroscopy, Chem. Phys. Let., 262, pp. 105, 1996.

* cited by examiner

Primary Examiner—Richard A. Rosenberger
(74) Attorney, Agent, or Firm—Lumen Intellectual Property Services, Inc.

(57) ABSTRACT

An ring-down spectroscopy instrument comprising a ring-down cavity (RDC) and CW light source (CWLS). The CWLS produces light having components with different polarizations. The ring-down cavity is optically isolated from the light source so that light reflected from the cavity is precluded from perturbing the light source. A frequency shifter shifts a mean frequency of the first component of input light with respect to a mean frequency of the second component of input light by a frequency shift $\Delta v$. A first detector measures a signal beam with the a polarization. A second detector measures a tracking beam having a second polarization. The frequency shift $\Delta v$ is equal to a difference between a resonant frequency of a first cavity mode with the first polarization and a resonant frequency of a second cavity mode having the second polarization. A threshold detector delivers a trigger pulse to the frequency shifter when an intensity of the signal beam reaches a predetermined value. The trigger pulse causes the frequency shifter to temporarily change the frequency shift $\Delta v$, thereby temporarily decoupling the first component of input light from the ring-down cavity. An embodiment of the invention includes a ring down spectroscopy method. Radiation coupled into a ring-down cavity is swept in frequency by to excite one or more resonant modes of the cavity. When a fundamental mode of the cavity reaches a predetermined threshold value a digitizer produces a ring-down decay curve. An absorption spectrum is determined by extrapolating a decay constant from a logarithm of the decay curve.

53 Claims, 8 Drawing Sheets

SWEPT CONTINUOUS WAVE CAVITY RING-DOWN SPECTROSCOPY

CROSS-REFERENCE TO RELATED APPLICATIONS

This application is based on Provisional application No. 60/114,441 filed Dec. 31, 1998, which is herein incorporated by reference.

U.S. GOVERNMENT RIGHTS

This invention was made with the support of the U.S. Government under grant no. DE-FG03-92ER14304. The U.S. Government has certain rights in this invention.

FIELD OF THE INVENTION

The present invention relates to absorption spectroscopy, and more particularly to a method and apparatus for performing ring-down spectroscopy using a continuous wave light source and using two polarizations of light in a cavity.

BACKGROUND ART

Cavity ring-down spectroscopy (CRDS) is a general, high sensitivity technique for measuring absorption. CRDS has been primarily applied to the study of very weakly absorbing species or dilute species concentrations. In CRDS, monochromatic light from a laser is injected into a high finesse optical resonator, called a ring-down cavity (RDC), which encloses a sample. When the light source is abruptly terminated, light trapped inside the RDC decays due to finite resonator losses and can be monitored by detecting light transmitted through a mirror of the RDC. Typically, the light exiting the RDC decays exponentially in time with a decay time constant $\tau$, called the ring-down decay constant. The rate of decay, called the ring-down rate (RDR) is directly proportional to resonator losses due to transmission, scattering, diffraction, absorption etc., and absorption by sample species at a particular wavelength. The RDR is inversely proportional to $\tau$. A spectrum of the sample species is obtained by measuring the RDR as a function of wavelength.

CRDS has been performed using both pulsed and continuous wave (CW) laser sources. Pulsed CRDS (P-CRDS) suffers from several limitations. Because the pulse duration is typically less than several RDC round-trip times, no energy buildup can occur in the optical resonator. The RDC output is therefore severely attenuated at the cavity output. This attenuation produces weak output signals with inferior signal to noise characteristics. Furthermore, many pulsed laser sources have repetition rates lower than 1 kHz, which preclude real-time spectral acquisition and extensive averaging to improve signal-to-noise ratio. Furthermore, most pulse laser sources have line-widths exceeding hundreds of kHz for nanosecond pulses (even when Fourier-transform-limited), which limits the spectral resolution of the CRDS technique.

Recently, efforts have been made to overcome most of these limitations by the use of narrow band (<10 MHz) CW lasers. By coupling the CW laser into the high finesse RDC, light inside the RDC is built up, and cavity throughput increases. In principle, cavity throughput can become close to 1.0, allowing shot-noise-limited detection, as demonstrated by Zare and co-workers in 1998. Much current laser ring-down spectroscopy is still performed with fairly costly laser sources, e.g. Ti:Sapphire lasers, optical parametric oscillators, and external cavity diode lasers. The advent of laser diodes as CW laser sources dramatically decreased the cost of CRDS based laser systems. Semiconductor laser diodes can potentially provide inexpensive laser sources for CW-CRDS as they rapidly improve in power, wavelength coverage, and reliability.

Diode lasers are CW sources with relatively weak output powers, e.g., a few milliwatts (mW). If a CW diode laser is modulated with a small duty cycle (i.e., shorter than the cavity roundtrip time), resonator interference effects and the need to frequency match the laser to a narrow cavity resonance, can be eliminated. Unfortunately, only very small cavity throughput can be achieved this way, which results in very noisy signals.

For example, a high finesse resonator constructed with 99.999% reflecting mirrors attenuates any input by about $10^{-10}$. The injection of a 1 mW pulse of non-mode-matched CW radiation would result in $10^{-13}$W of light power at the beginning of the ring-down decay waveform. Such a signal is virtually impossible to detect with a broadband photodetector, particularly in the infrared where photomultipliers are generally ineffective. To record ring-down decay transients with decay constants of order 1 microsecond, a 1 MHz bandwidth, $10^{-14}$ W/Hz$^{1/2}$ noise equivalent detector is typically necessary and a detector noise of about $10^{-11}$ is calculated. The noise, which is inherent in the detection process, is significantly larger than the ring-down signal power at any point in the waveform.

If the laser is locked to one of the cavity resonances over the course of several decay constants, and the laser linewidth is smaller than the cavity resonance, then substantial buildup of the intracavity field can occur. Consequently, strong ring-down signal can be observed after the laser beam is quickly terminated, i.e. faster than $\tau$. The cavity throughput may become close to 1.0, which allows shot-noise limited detection of the ring-down signal. Shot-noise-limited detection of several mW of light can produce high signal-to-noise ratios, on the order of 1,000,000:1.

Laser diode sources typically have linewidths broadened by high frequency jitter to about 10 MHz. This is significantly larger than the typical ring-down cavity linewidth of a few kHz. Classical error signal extraction is, therefore, extremely difficult, The problem of locking a laser and a super-cavity is illustrated in FIGS. 1$a$ and 1$b$. FIG. 1$a$ illustrates locking an ordinary low finesse cavity and laser together. In this case, the laser linewidth is much smaller than the cavity linewidth. Frequency modulation of the laser typically causes modulation of the intensity of light transmitted through the cavity. The amplitude of this intensity modulation, which represents a form of error signal, is generally proportional to the frequency detuning of the laser with respect to the cavity resonance frequency. The phase of the intensity modulation changes sign when the laser passes from a frequency less than the cavity resonance frequency to a frequency greater than the cavity resonance frequency. The error signal is zero if the laser line is centered on the cavity resonance frequency. If this error signal is demodulated, amplified and applied to the element that changes the laser frequency, the laser will be kept in resonance with the cavity.

When the same laser is locked to a very high finesse cavity, the effective laser linewidth is typically much larger than the cavity resonance frequency, as shown in FIG. 1$b$. The instantaneous frequency changes very rapidly over a spectral range several orders of magnitude larger than the laser linewidth. The duration of the laser center frequency changes can be as short as a few microseconds, so that the laser frequency changes essentially instantaneously.

Because the response time of the a ring-down cavity depends on the bandwidth of its frequency changing element, typically a piezo-electric transducer (PZT), most cavities can respond at low kHz rates. In this case, no distinct error signal will be produced from this cavity and the "simple" servo-loop won't work.

In principle, the signal error problem can be overcome using the Pound-Dever locking technique and feedback to an electro-optic or acousto-optic modulator to change the laser frequency of laser light reaching the ring-down cavity. However, these systems require extreme mechanical stability and, for practical systems, a very large locking bandwidth. Furthermore, if the laser light is extinguished, e.g., to measure the decay constant, the Pound-Dever lock would be lost. The locking servo becomes ineffective after each decay waveform measurement, which introduces long system recovery times. Furthermore, strong mechanical perturbations might cause the laser to re-lock to a cavity resonance separated in frequency from the previous resonance. At best, such a locked system would be intermittently usable for recording absorption lines of specific species in real-time, e.g. a concentration measurement every few seconds.

An alternative method for locking a laser diode (LD) to a high finesse cavity utilizes optical feedback. In this method, a small fraction of the laser radiation already accumulated inside the cavity is sent back to the diode laser. The distance between the LD and the cavity input mirror is adjusted so that the feedback radiation is in phase with the laser radiation. As a result, optical feedback takes place, which substantially reduces the LD linewidth. Ultimately, the laser linewidth can be reduced to much less than the cavity resonance linewidth. Substantial intensity also builds up inside the cavity. This works well with a relatively low finesse cavity when the LD is locked to the cavity and never turned off.

In CW-CRDS, the light source must be extinguished to measure the ring-down decay waveform. Consequently the optical feedback method encounters the same locking electronics problem as the Pound-Dever method. In the optical feedback case, a servo-loop needed to keep the feedback signal in phase with the laser radiation may be perturbed and driven out of phase thus converting positive feedback to negative feedback. Consequently, the system may re-lock onto an arbitrary cavity mode resulting in intermittent operation. Both the optical feedback system and Pound-Dever system must be mechanically stabilized with interferometric precision. Therefore, neither system can be easily implemented in environments having large mechanical perturbations. Furthermore, the optical feedback locking technique cannot be effectively used for CW sources other than LDs. Even under optical isolation, the optical feedback often results in phase fluctuations and mode hopping of the LD, so that the laser can not be relocked to the same cavity mode from shot to shot. These problems result in unreliable operation of CW-CRDS systems and preclude the demonstration of compact, LD-based, CW-CRDS systems.

There is a need, therefore, for a cavity ring down spectroscopy system that provides highly sensitive absorption measurements in an environment of serious external mechanical perturbations.

OBJECTS AND ADVANTAGES

Accordingly, it is a primary object of the present invention to provide a spectroscopy tool that can be used for ultra-sensitive, real-time detection of samples inside optical cavities. It is a further object of the invention to provide a high finesse optical resonator that is excited by a CW single-frequency light source and optically isolated from the resonator. Another object of the invention is to provide a means to ensure that the cavity resonance follows the light source as the light source frequency is swept over an arbitrarily large spectral interval. It is an additional object of the invention to provide means to automatically recover after a strong mechanical perturbation, which may bring the center frequency of the cavity resonance far away from the actual light source frequency.

The above objects and advantages are attained by an instrument comprising a high finesse optical resonator, such as a ring-down cavity (RDC), a single-frequency CW light source (CWLS), a frequency shifter and first and second detectors. The CWLS produces input light having a first component with a first polarization and a second component having a second polarization. Suitable optics couple the input light into the resonator. The ring-down cavity typically has a first mirror and a second mirror. A translator controllably moves the first mirror. The ring-down cavity is optically isolated from the light source so that any light reflected from the cavity is precluded from perturbing the light source. The frequency shifter shifts a mean frequency of the first component with respect to a mean frequency of the second component by a frequency shift $\Delta v$. The first detector is configured to measure an intensity of a signal beam with the first polarization exiting from the ring resonator. The second detector is configured to measure an intensity of a tracking beam having the second polarization exiting from the ring resonator. The frequency shift $\Delta v$ is equal to the difference between a first resonant frequency of the resonator corresponding to a first cavity mode with the first polarization, and a second resonant frequency corresponding to a second cavity mode having the second polarization.

A tracking circuit determines an oscillating voltage from a signal received from the second detector. The oscillating voltage drives the translator to oscillate the first mirror around a central value corresponding to a resonant coupling between said ring resonator and the first component of input light. A threshold detector delivers a trigger pulse to the frequency shifter when an intensity of the signal beam reaches a predetermined value. The trigger pulse causes the frequency shifter to temporarily change the frequency shift $\Delta v$, thereby temporarily decoupling the first component of input light from the ring resonator.

The instrument measures the cavity time delay as a function of source wavelength to obtain an absorption spectrum of a medium inside the cavity. The system is insensitive to mechanical perturbations because the cavity does not provide any reflected light to the light source. The frequency stability and reproducibility of the light source determine the frequency stability and reproducibility of the instrument.

The instrument also includes means to ensure reliable and reproducible injection of light source radiation into the cavity. The instrument tracks cavity resonance as it is swept in frequency across the light source laser line. The tracking ensures that the cavity and light source frequencies are always close to each other.

An embodiment of the present invention includes a ring down spectroscopy method. The method couples radiation from a continuous-wave light source (CWLS) into a ring-down cavity. The radiation is swept in frequency by an RDC length, e.g., one or more free spectral ranges of the cavity, to excite one or more resonant modes of the cavity. A threshold detector is triggered when a fundamental mode of the cavity reaches a predetermined threshold value. The threshold detector then triggers a digitizer to sample a ring-down decay curve. A processor stores the points of a waveform generated from the decay curve. A point on an absorption spectrum can be determined by extrapolating a decay constant from a logarithm of the waveform points. A portion of an absorption spectrum can then be determined by iteratively repeating the method while tuning the CWLS over a given frequency or wavelength range.

DETAILED DESCRIPTION

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

Figure 2:
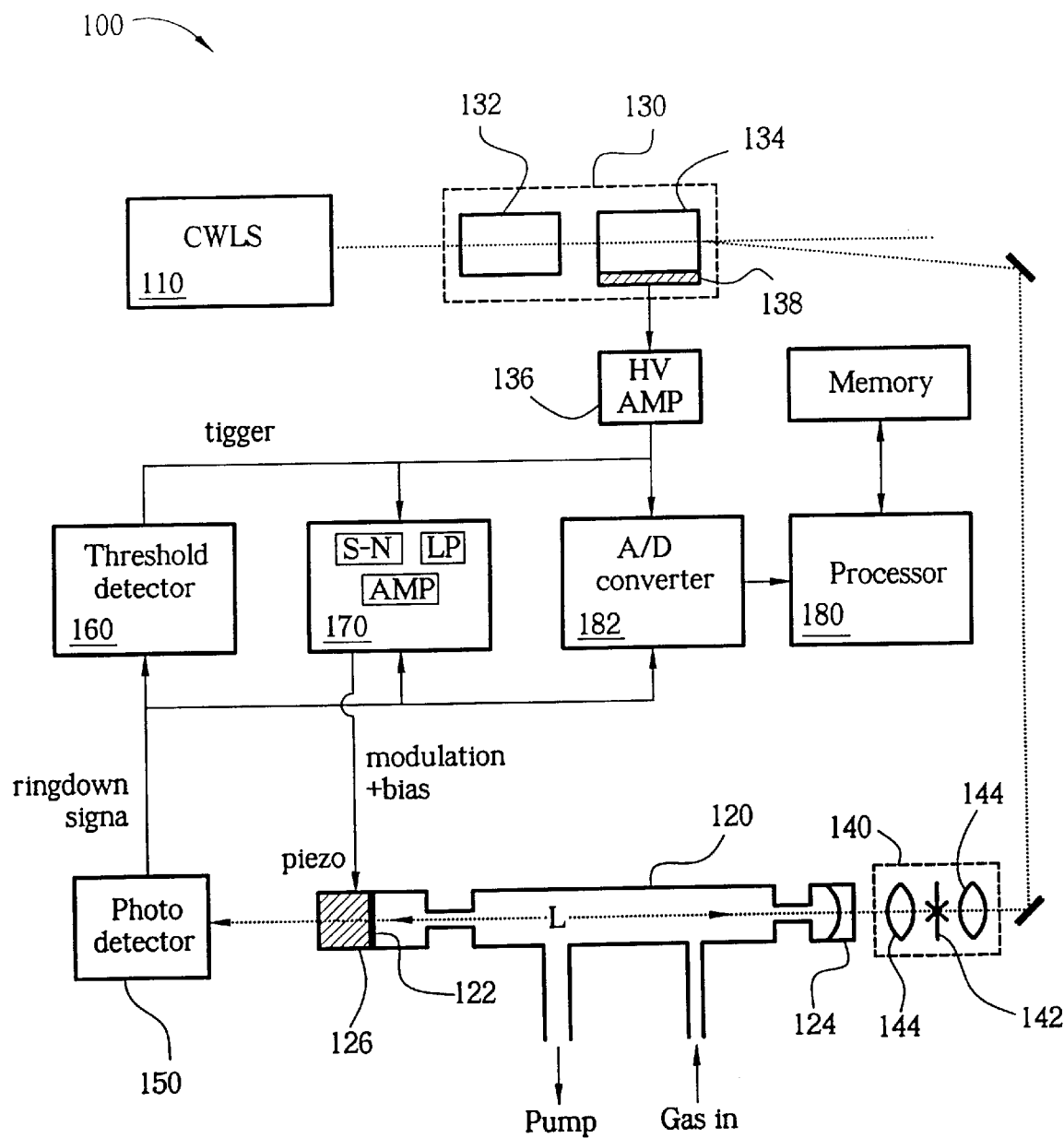
FIG. 2 depicts a schematic diagram of a ring-down spectroscopy instrument according to a first embodiment of the present invention.

FIG. 2 illustrates a ring-down spectroscopy instrument according to a first embodiment of the present invention. The instrument 100 generally comprises a continuous wave light source (CWLS) 110, an optical ring-down cavity 120, an optical isolator 130, mode-matching optics 140 a photo-detector 150, a threshold detector 160, a cavity tracking circuit 170 and a processor unit 180. Radiation from CWLS 110 couples into cavity 120. CWLS 110 can be any type of CW light source such as a CW single longitudinal and transverse mode tunable laser. In a preferred embodiment, CWLS 110 is a single frequency tunable external cavity diode laser, such as a diode laser model 6124 manufactured by New Focus, of Santa Clara, Calif. Alternatively CWLS 110 may be a distributed feedback (DFB) laser diode manufactured, e.g., by Sensors Unlimited of or Polyus Research Corporation of Moscow, Russia. CWLS 110 provides a single frequency tuning range, e.g. 765 to 790 nm, with several mW, e.g., 1 to 20 mW, of power output. Cavity 120 is a linear Fabry-Perot resonator, having two mirrors 122. By way of example, mirrors 122 may be spherical "supermirrors" manufactured by Research Electro Optics of Boulder, Colorado, each having a radius of curvature r=45 cm, and covering a broad spectral range, e.g. from, 720 nm to 820 nm. The reflectivity of supermirrors exceeds 99.9% and is usually better than 99.99%. Mirrors 122, 124 are placed at least a distance L of 45 cm apart, close to the value of L=1.5r. A distance L=1.5r provides a triply degenerate cavity with the modes split into three groups equally spaced within the free spectral interval of the cavity. For cavity mirror losses on the order of 1–9.7 parts per million (ppm) the reflectivity of mirrors 122, 124 is between 99.99775% and 99.9999% when the cavity is evacuated. At least one of the mirrors 122, 124 is translatably mounted to allow the length L of cavity 120 to be varied by several microns. For example, translational motion may be implemented by mounting mirror 122 to a piezo-electric transducer (PZT) 126.

Optical isolator 130 isolates CWLS 110 from cavity 120. By way of example, isolator 130 comprises a Faraday isolator 132 and acousto-optic modulator (AOM) 134. A suitable Faraday isolator is manufactured by LEYSOP LTD, of the United Kingdom. The Faraday isolator is optional, and can be omitted in other embodiments when the CWLS is not sensitive to optical feedback, as in the case of a Ti:Sapphire laser or single frequency dye laser. AOM 134 performs two functions. First, it shifts the optical frequency of the radiation reflected from cavity 120 by twice the value of a driving frequency, thereby providing optical isolation. Second, AOM 134 acts as a switch to turn the radiation from CWLS 110 on and off so that ring-down may be observed. AOM 134 is used in the deflection mode to optically couple the deflected beam to cavity 120. Other methods that can switch radiation from CWLS 110 include electro-optic modulators, current modulation input to CWLS 110 or, in the case of a diode laser, a transistor that shorts the diode laser to ground.

Radiation from CWLS 110 must also pass through mode-matching optics 140 before entering cavity 120 to guarantee single-transverse and longitudinal mode excitation in cavity 120. In a preferred embodiment, the mode-matching optical system comprises a 50 micron diameter pinhole 142 and two lenses 144 with 50 cm focal lengths.

Photodector 150 detects radiation exiting cavity 120, called a ring-down signal. Photodetector can be any type of low noise photodetector. In a preferred embodiment, photodetector 150 is a Si or InGaAs PIN photodiode. An output signal of photodetector 150 is coupled to threshold detector 160, which generates a trigger signal as soon as the output signal of cavity 120 exceeds a predefined adjustable level. The trigger signal controls cavity tracking circuit 170, and initiates analog to digital conversion of cavity ring-down signals by a digitizer 182 in processor unit 180. Digitizer 182 may be an analog to digital converter of any known type. In a preferred embodiment, digitizer 182 is a 1 MHz 12 bit PC interface card, model CIO-DAS 16/M1 manufactured by computer boards, Inc. of. In addition to digitizer 182, processor unit also includes a memory 184, and a timer 186. Processor unit 180 may be a microprocessor system of any known type. In an exemplary embodiment processor unit 180 is a 486DX33 personal computer. Ring-down spectroscopy system 100 operates as described below. A beam of radiation from CWLS 110 is aligned to cavity 120 such that during an RDC length seep, i.e. a sweep in frequency by a few free spectral ranges of cavity 120, successively excited cavity resonances can be recorded on an oscilloscope connected to photodetector 150. Three groups of cavity modes that are equally spaced within the spectral range are typically observed. The first group contains a fundamental $TEM_{00}$ cavity mode, the second group contains a $TEM_{10}$ cavity mode and the third group contains a $TEM_{02}$ cavity mode. Each group may also contain higher order modes, which are typically very closely spaced in frequency within every particular group in a nearly degenerate optical cavity. Mode matching optics 140 are then aligned so that the excitation efficiency of all higher modes is significantly, e.g. 20 to 100 times, reduced compared to the fundamental $TEM_{00}$ cavity mode. It is important that a configuration of cavity 120 is close to that of a degenerate case. In a preferred embodiment, a triply degenerate cavity configuration is used, with cavity length $L\approx1.5r$. However, for one skilled in the art, it is evident that other triply degenerate cavity configurations, such as $L\approx0.5r$ can also be used. Alternatively, cavities other than triply degenerate, such as double degenerate (nearly confocal) or cavities with higher degrees of degeneracy (four five, etc) can be used in other embodiments. A skilled artisan will also understand that other types of high finesse optical cavities can be used in other embodiments, such as ring cavities composed of three, four, or more mirrors, V-shaped cavities or any other type of stable resonator cavity.

Once the cavity is aligned and mode-matched, the amplitude of the modulation applied to the modulator 134 is decreased so that the modulation amplitude becomes less than one free spectral range of cavity 120. Threshold detector 160 is adjusted so that it is only triggered when a substantial buildup of the $TEM_{00}$ mode in cavity 120 is achieved. The threshold value of threshold detector 160 is typically set high enough so that weaker buildups in the higher order mode groups generally cannot trigger threshold detector 160. Such a threshold level ensures only the $TEM_{00}$ mode ring-down events are observed, thereby providing purely exponential decay signals free of any transverse mode beating. The trigger signal produced by threshold detector 160 triggers digitizer 182 which samples a ring-down decay curve. A large number of waveform points is generated and stored in processor memory 184. Processor unit 180 fits a straight line to the logarithm of the recorded ring-down waveform to extrapolate a decay constant. Processor unit 184 can also average a predefined amount of decay events in order to improve the measured signal to noise ratio and send a command to CWLS 110 to tune to the next frequency. By tuning CWLS 110 over the required frequency (or wavelength) range, a portion of the absorption spectrum can be recorded.

Figure 3:
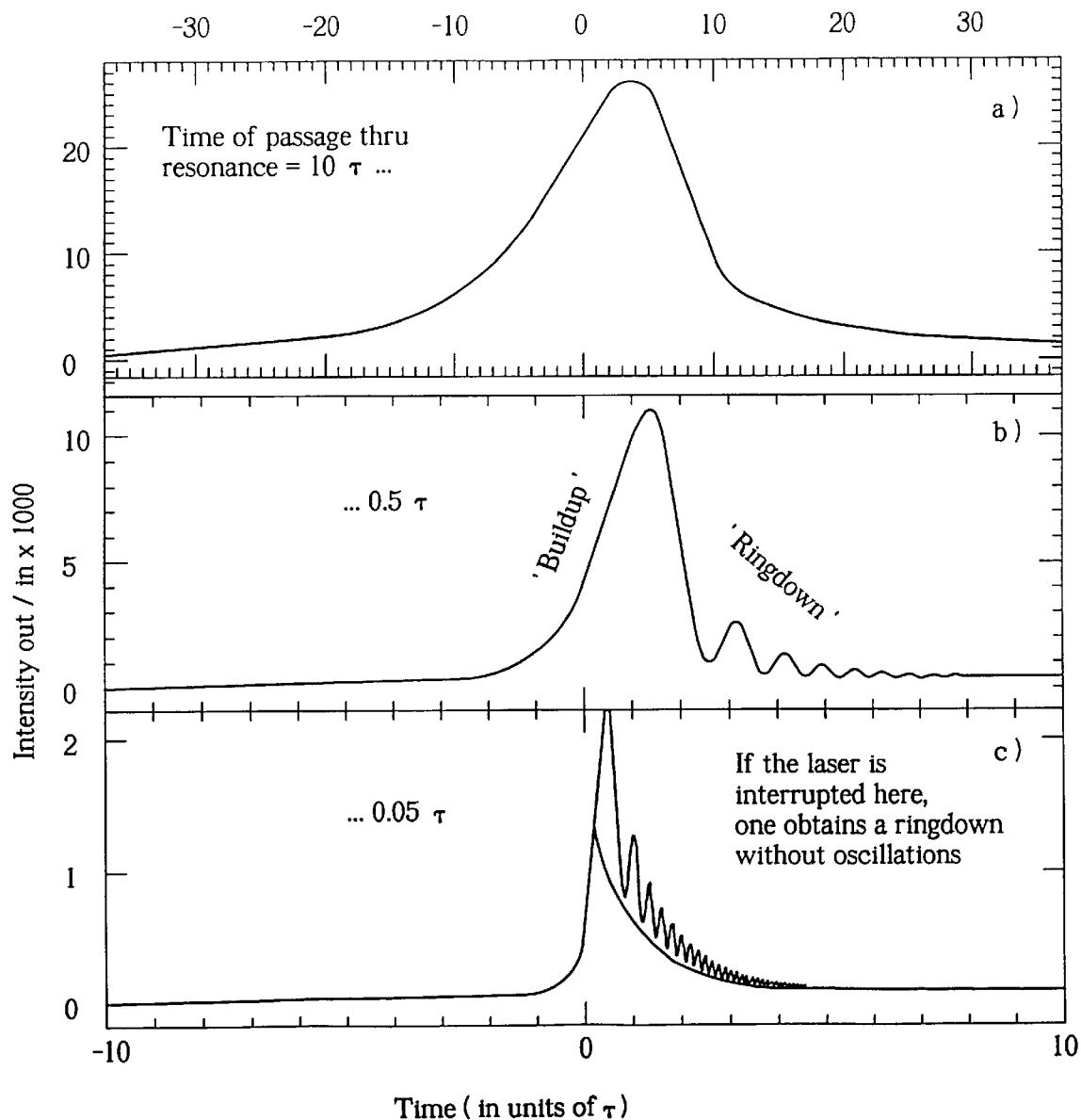
FIG. 3 illustrates the excitation process of a ring-down cavity with a CWLS when the frequency of the cavity resonance is swept.

FIG. 3 illustrates the excitation process of a high-finesse ring-down cavity (RDC) with a CWLS when the frequency of the cavity resonance is swept. The top two graphs in FIG. 3 depict the calculated cavity response when the speed of the sweep through resonance is continuously increased. The interaction of the intracavity field with the incoming radiation can cause high-frequency oscillations or distortion of the RDC transient response. Slower sweep speeds of the cavity resonance peak through the laser line produce higher buildup intensities. If the incoming radiation is switched off when substantial buildup has been achieved inside the RDC a clean exponential decay will be observed as shown in the bottom graph of FIG. 3. For this reason, the trigger pulse is also used to switch off the CWLS radiation, e.g., using an acousto-optic deflector in the preferred embodiment.

Figure 4:
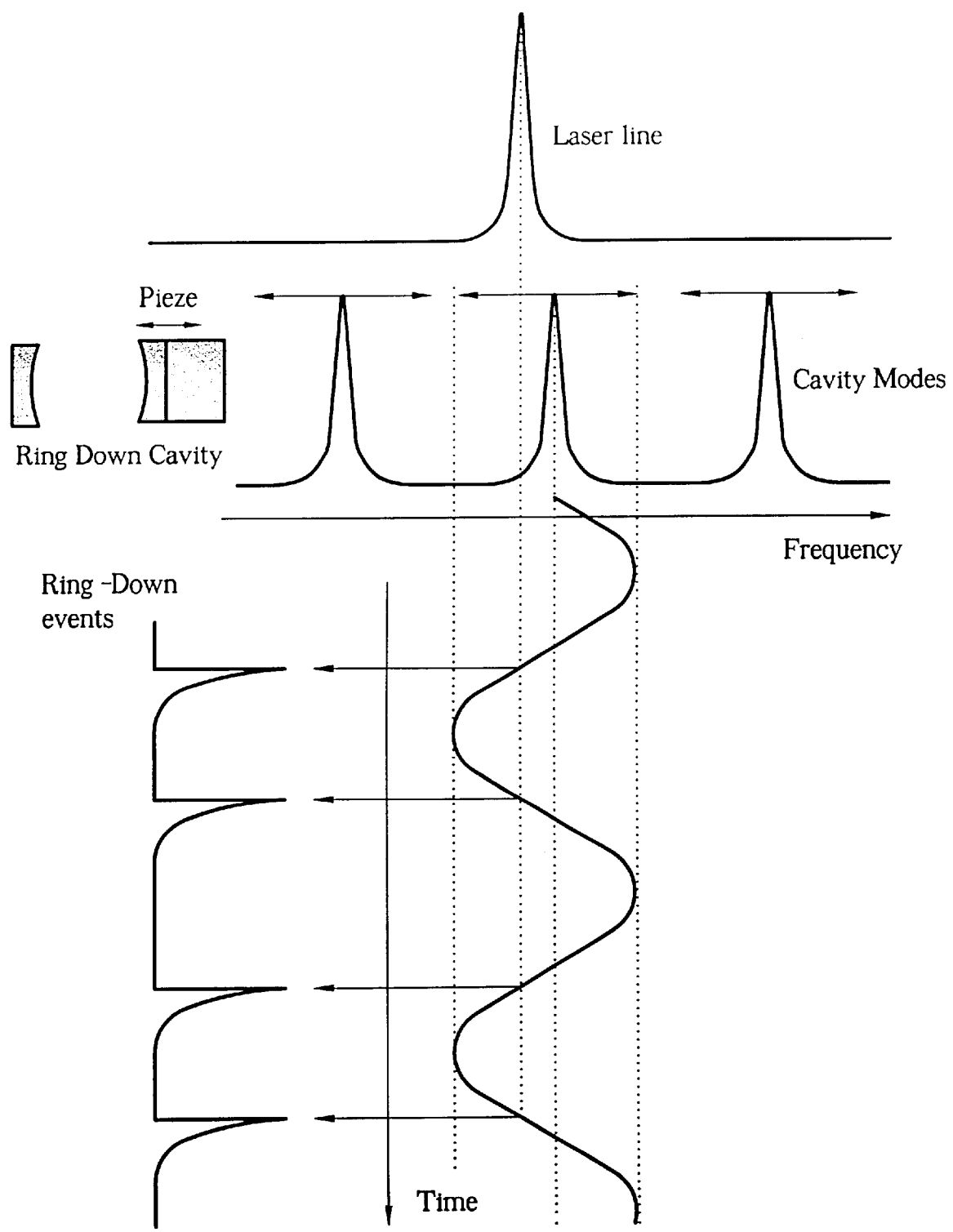
FIG. 4 illustrates the operation of a tracking circuit used in an embodiment of the instrument of the present invention.

Tracking circuit 170 generally comprises a sample and hold circuit 172 a low-pass filter 174, and an amplifier 176. FIG. 4 illustrates the operation of tracking circuit 170. The cavity length may be sinusoidally swept around the laser line by applying a sinusoidal voltage having a frequency of a few hundred Hz to a high voltage amplifier 136 that drives a PZT 138 in modulator 134. The laser line shown in FIG. 4 is slightly displaced to lower frequencies with respect to the center position of the cavity modulation. In this case the ring-down events occur at the negative points of modulation voltage. Trigger pulses from threshold detector 160 corresponding to ring-down events are used to trigger a sample and hold circuit 172, which samples the values of the modulation voltage. The output of sample and hold circuit 172 is then filtered by low-pass filter 174, amplified by amplifier 176, and sent to a summing input of PZT high voltage amplifier 136. The bias voltage of PZT amplifier 136 decreases and the center frequency of the cavity resonance moves closer to the laser line until all ring-down events occur in the vicinity of the zero modulation voltage. This tracking ensures that the resonance of cavity 120 will follow a laser line of CWLS 110. A bias of PZT amplifier 176 is automatically maintained at a value such that RDC modulation is performed symmetrically around the laser line. This tracking method is insensitive to external mechanical perturbations of the cavity 120 because the stable laser line position is used as a reference.

When CWLS 110 is scanned in frequency, cavity 120 follows it until the maximum or the minimum voltage of amplifier 176 is reached or exceeds the PZT safe operating limit. At this point tracking circuit 170 can no longer track CWLS 110. In this case, the maximum scanning range of the spectrometer would be limited by the maximum excursion of PZT 138, which corresponds to a few free spectral ranges of cavity 120, typically several GHz. This scan range limitation can be surmounted by measuring the bias voltage of amplifier 176 at each frequency with a second channel of digitizer 182. When the bias voltage approaches a predefined upper or lower threshold value, processor unit 180 generates a reset pulse to amplifier 136. T reset pulse resets the voltage of amplifier 136 to a value that changes the cavity length by an amount corresponding to shifting the mode of cavity 120 by an integral number of free spectral ranges. Injection of radiation from CWLS 110 into the next set of modes of cavity 120 is thereby established. Arbitrarily long scans can be performed automatically with PZT 138 being operated within its range of linearity.

The tracking described above will work as long as the laser line from CWLS 110 remains within the sweep range of cavity 120. If a strong perturbation occurs such that the laser line is knocked out of the sweep range, then no buildup events occur during the sweep, and sample and hold circuit 172 will not be activated. No tracking occurs until the length of cavity 120 drifts into a position where the cavity sweep interval and laser line intersect. To avoid large dead times associated with this situation, spectroscopy system 100 may be configured for fast recovery. For example, timer 186 of processor unit 180 is set with a predetermined time constant every time a cavity ring-down event is detected and processed. If no ring-down event occurs within the specified interval, tracking circuit 170 is assumed to be in a dead state. In this case, a linear ramp is applied to the bias voltage input to amplifier 136. The ramp change the length of cavity 120 linearly in time until the laser line and cavity sweep range intersect. At this point, ring-down events resume and tracking circuit 170 returns to normal operation.

Figure 5:
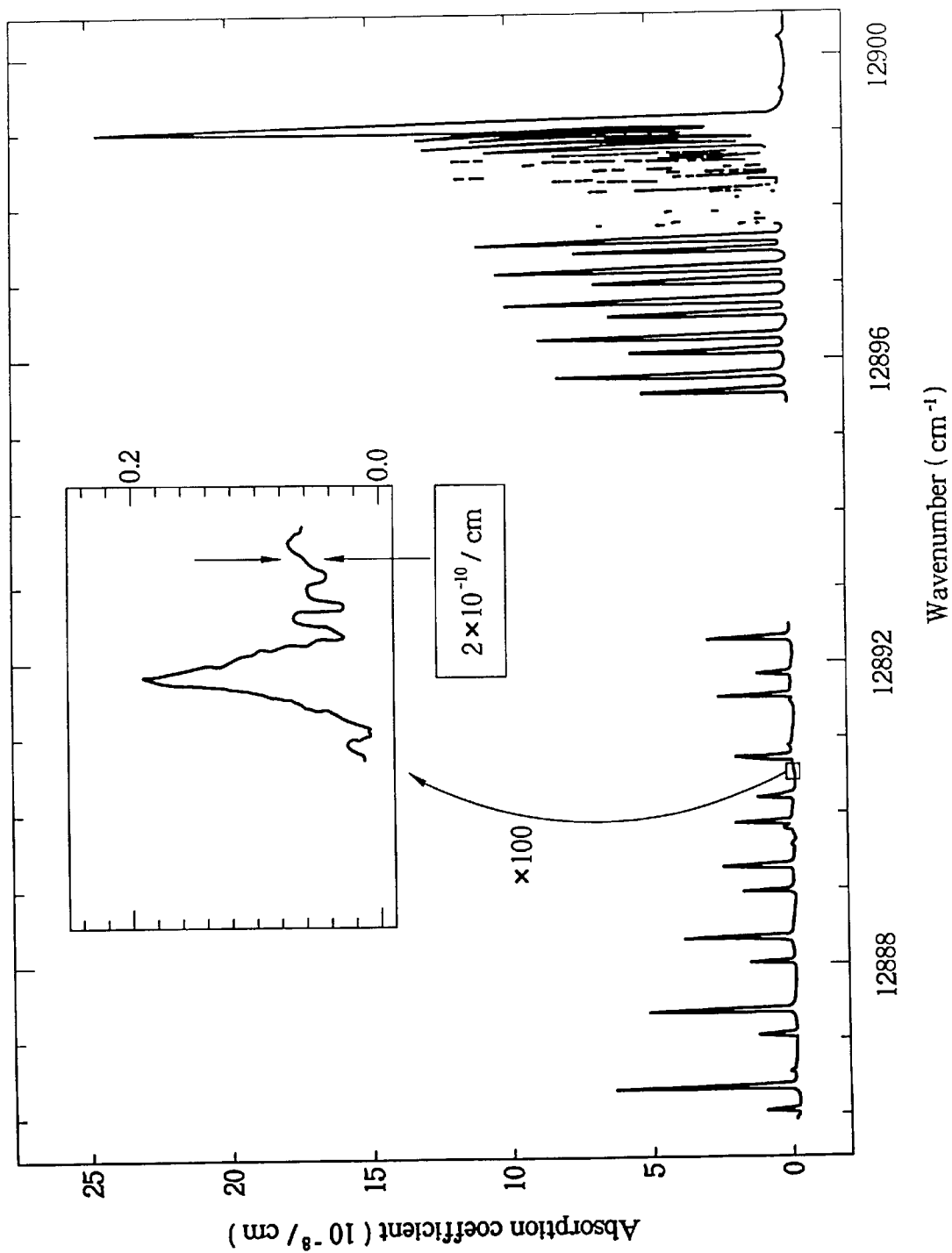
FIG. 5, depicts an absorption spectrum of $N_2O$ molecules obtained with a spectrometer of the type shown in FIG. 2.

A cavity ring-down spectrometer of the type described above with respect to FIG. 2 has been operated under different experimental conditions. The spectrometer is capable of working automatically without realignment or reactivation by an operator over the course of many hours. Furthermore, the spectrometer operates as soon as laser radiation is present. FIG. 5 depicts an example of an absorption spectrum obtained with such a spectrometer. The spectrum represents the $6v_3\Sigma - \Sigma$ bond of $N_2O$ molecules cooled in an RDC absorption cell at 30 torr pressure and room temperature. The rms-noise equivalent absorption coefficient is about $2 \times 10^{-10}$/cm.

Figure 6:
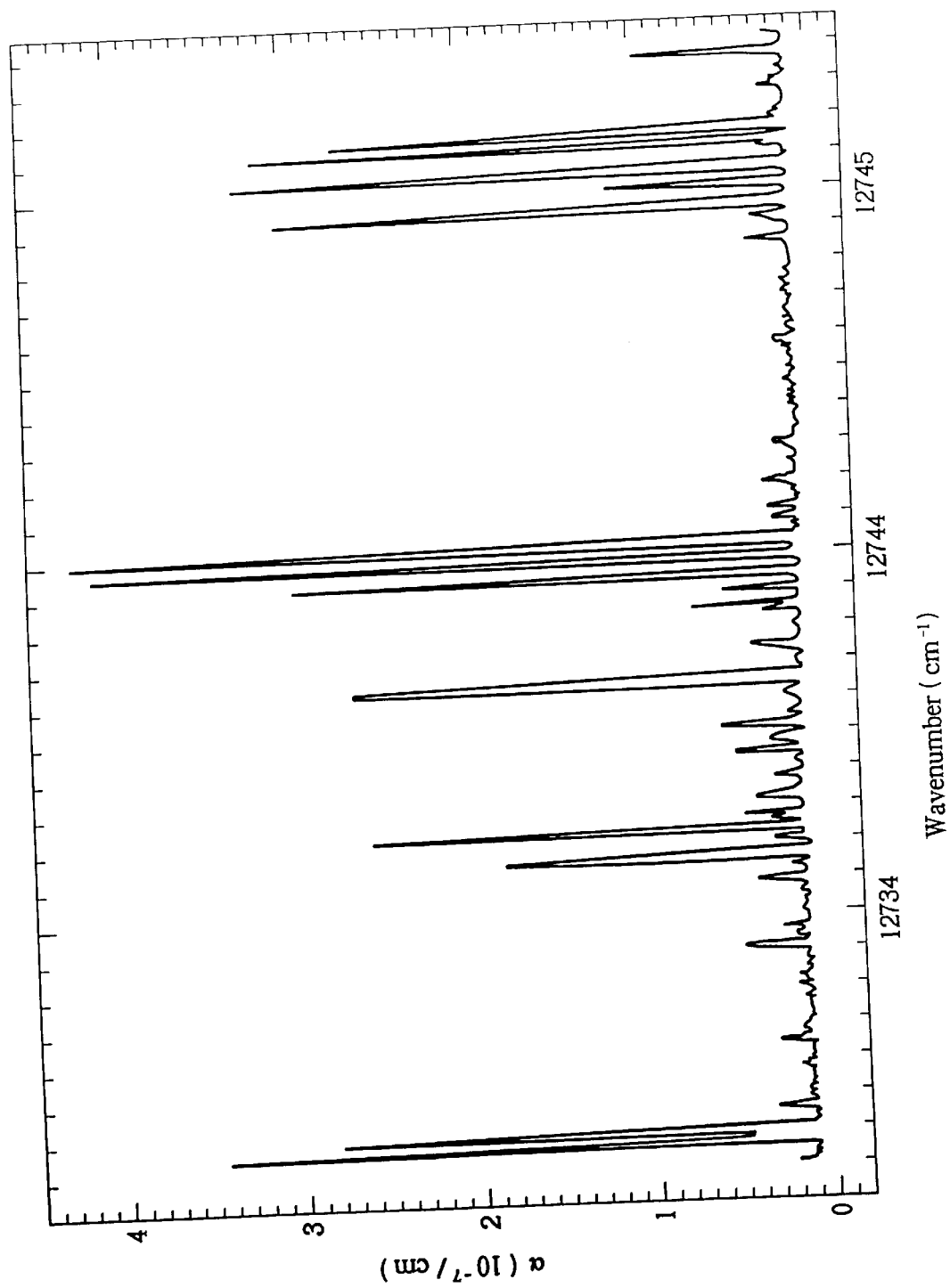
FIG. 6, depicts an absorption spectrum of $NO_2$ molecules cooled in a supersonic slit jet obtained with a spectrometer of the type shown in FIG. 2.

The stability of the spectrometer is illustrated by FIG. 6, which depicts an absorption spectrum of $NO_2$ molecules cooled in a supersonic slit jet. Strong mechanical perturbations from the roots pump used to evacuate the supersonic jet chamber had little or no effect on the operation of the spectrometer.

Figure 7:
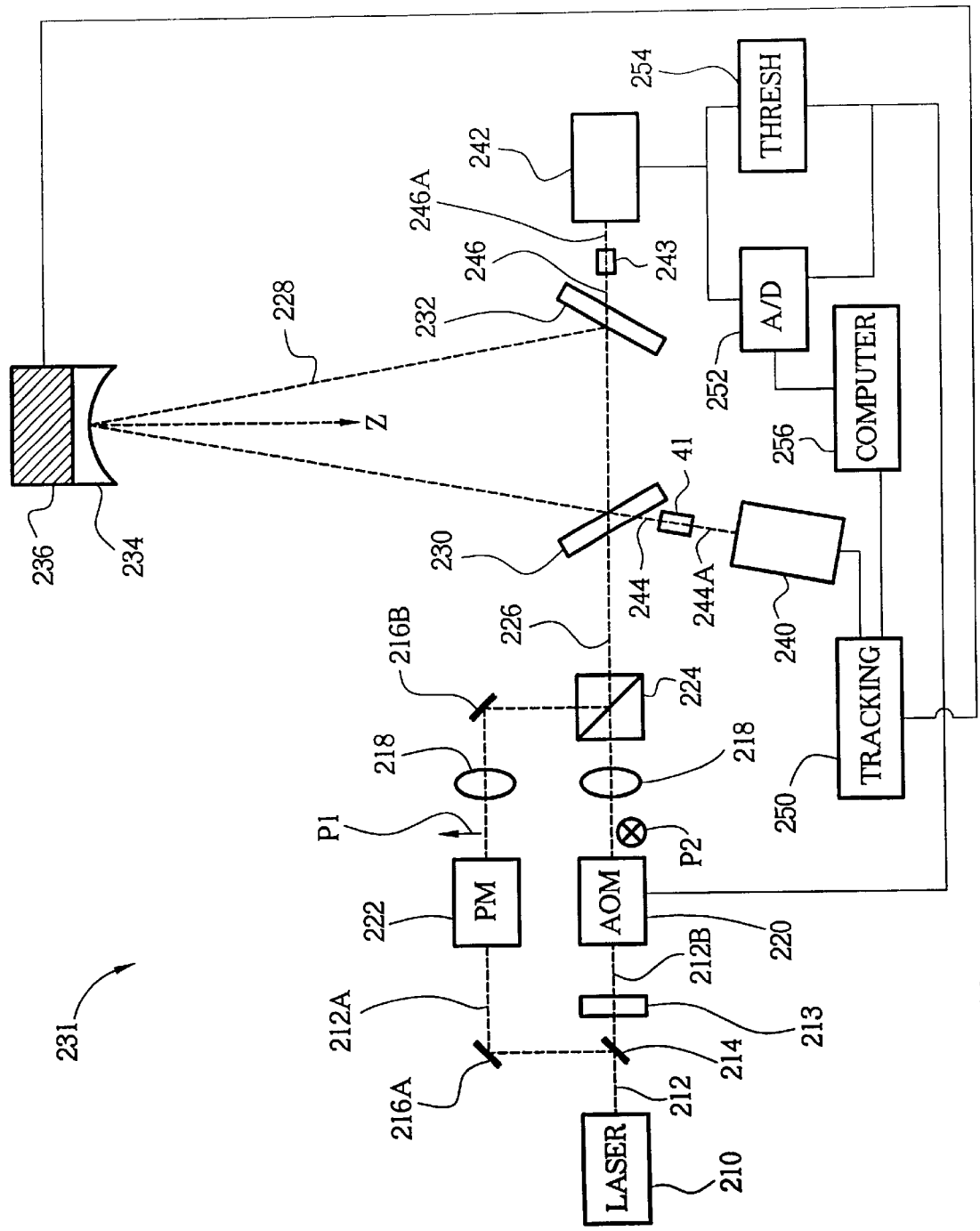
FIG. 7 depicts a schematic diagram of a ring-down spectroscopy system according to a second embodiment of the present invention.

A ring-down spectroscopy system according to a second embodiment of the invention is shown in FIG. 7. The system 200 generally comprises a light source 210, a beam splitter 214, a half-wave plate 213, mirrors 216A, 216B, a modulator 220, a ring resonator 231, a detector 240, and a tracking circuit 250.

Light source 210 is typically a monochromatic light source, such as a laser. Light source 210 emits a continuous wave (CW), beam 212. Light source 210 is preferably a single frequency tunable external cavity semi-conductor laser, for example a New Focus diode laser model 6124, or a distributed feedback laser diode, such as is available from Sensors Unlimited and from Polyus Research Corporation. Light source 210 provides a single frequency tuning range, for example from 765 to 790 nm, with several milliwatts of output power, for example between 1 and 20 mW.

Figure 1A:
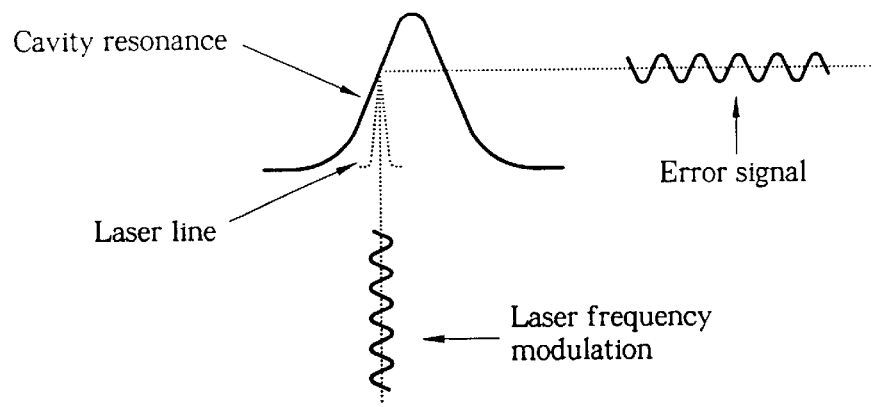
FIG. 1a illustrates locking to a low-finesse cavity of the prior art.
Figure 1B:
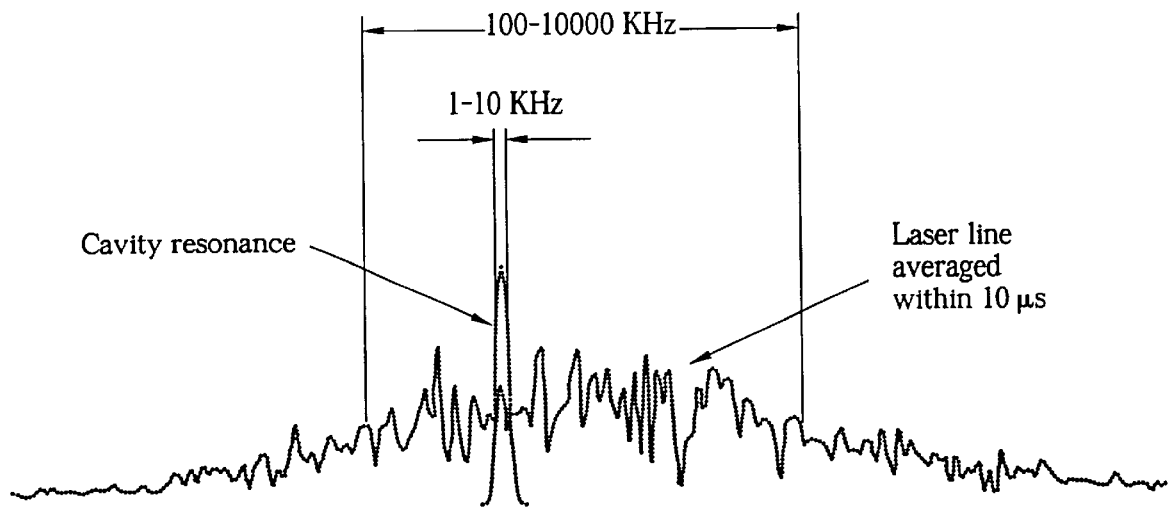
FIG. 1b illustrates an attempt to lock to a super cavity of the prior art.

Beam 212 is divided by a beam splitter 214 into two beams 212A and 212B. Beam 212B subsequently passes through a half-wave plate 213. After passing through the half-wave plate, beam 212B has a polarization P2 that is perpendicular to a polarization P1 of beam 212A. In the preferred embodiment, polarization P1 of beam 212A is in the plane of the page of FIG. 1, and polarization P2 of beam 212B is perpendicular to the plane of the page of FIG. 1, as shown. A polarization in the plane of the page of FIG. 7 is called p-polarization, and a polarization out of the page of FIG. 7 is called s-polarization. In the preferred embodiment, therefore, beam 212A has p-polarization and beam 12B has s-polarization. In other embodiments, however, the reverse is true: beam 212A has s-polarization and beam 212B has p-polarization.

Light source 210, beam splitter 214, and half-wave plate 213 provide a means for producing continuous wave light that has two components, beams 212A and 212B, having different polarizations. Other means for producing beams 212A and 212B are known in the art and are used in alternate embodiments of the ring-down spectroscopy system.

Figure 8:
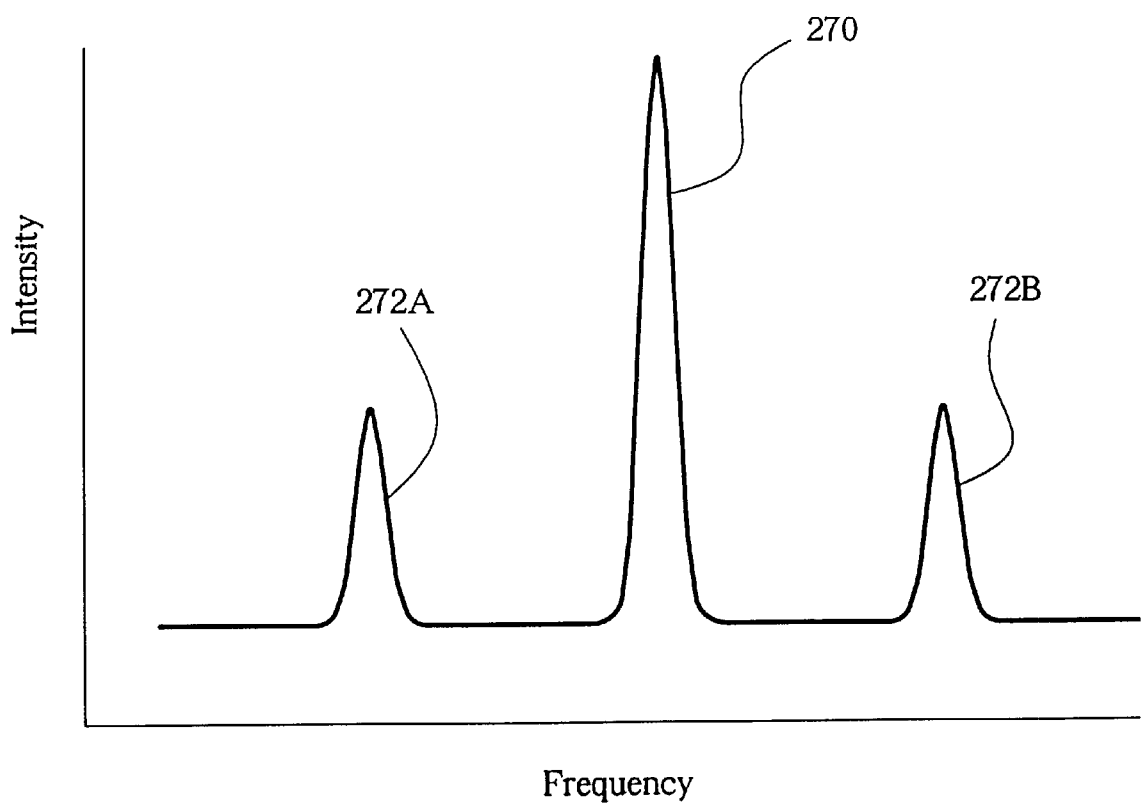
FIG. 8 is a plot of beam intensity versus frequency for a ring-down spectroscopy system of the type shown in FIG. 8.

A mirror 216A directs beam 212A to a phase modulator 222. The phase modulator induces side bands 272A and 272B on beam 212A, as shown in FIG. 8. Side bands 272A and 272B are produced symmetrically above and below a central frequency peak 270 of beam 212A. In the preferred embodiment, the mean frequency of each side band differs from the mean frequency of beam 212A by at least twice the linewidth (measured at half-maximum) of beam 212. The side bands are used for diagnostic purposes described later. In the preferred embodiment, phase modulator 222 is an electro-optic modulator.

Returning to FIG. 7, beam 212B passes through a modulator 220 that shifts the mean frequency of beam 212B by an amount $\Delta v$, and deflects the path of beam 212B slightly away from a straight line. After passing through modulator 220, beam 212B has a mean frequency that differs from the mean frequency of beam 212A by an amount $\Delta v$. In the preferred embodiment, modulator 220 is an acousto-optic modulator, or AOM.

Beams 212A and 212B are subsequently recombined using, for example, a mirror 216B and a polarizing beam splitter 224. Beams 212A and 212B combine to form a beam 226.

A ring resonator 231 comprises mirrors 230, 232, and 234. Beam 226 enters ring resonator 231 through mirror 230. Beam 226 then circulates around ring resonator 231 as an intracavity beam 228. Optical components 218 are used to efficiently couple, or mode match, beam 226 to ring resonator 231. Optical components 218 are known in the art and comprise, for example, pinholes and lenses. Appropriate lenses and/or pinholes to be included in optical components 218 may be calculated using Gaussian beam optics using, for example, the software package Paraxia. Optical components 218, mirrors 216A and 216B, and polarizing beam splitter 224 comprise optics that couple beam 226 into the ring resonator. Other optical configurations for such coupling are obvious and are used in alternate embodiments.

In the preferred embodiment, mirrors 230, 232, and 234 are highly reflective mirrors, often called "super mirrors", having a reflectivity greater than 99.9%, usually better than 99.99%. Such super mirrors are available from, for example, Research Electro Optics of Boulder, Colo. The mirrors preferably cover a broad spectral range, for example from 720 nm to 820 nm. Mirrors 230 and 232 are preferably planar on both the front and back sides; that is, mirrors 230 and 232 are preferably plano/plano mirrors. Mirror 234 is preferably a plano/concave mirror, having a concave surface facing the interior of ring resonator 231.

Intracavity beam 228 travels a round trip distance D from mirror 230 to mirror 232, then to mirror 234 and back to mirror 230. As an example of a presently preferred embodiment, round trip distance D is 42 cm, and the radius of curvature of mirror 234 is 100 cm.

Ring resonator 231 has a number of resonant modes. The frequency difference between adjacent $TEM_{00}$ modes is called the free spectral range, or FSR, and is equal to the speed of light divided by the round trip distance: $FSR=c/D$. Mirrors 230, 232, and 234 are preferably positioned so that the resonant modes of the ring resonator fall into two groups, with the $TEM_{00}$ mode separated from the $TEM_{01}$ and $TEM_{10}$ modes by half of the free spectral range. This separation facilitates single-mode excitation of the ring resonator by beam 226, particularly when light source 210 is a laser diode, which emits an asymmetric beam.

Intracavity beam 228 possesses both p- and s-polarizations, corresponding to light from beams 212A and 212B. As is well known from the physics of optical interfaces, s-polarized light non-normally incident upon a mirror acquires a phase when reflected, and this phase is different from the phase acquired by p-polarized light at the same angle of incidence. Therefore the interference conditions that define the resonant modes of ring resonator 231 for p-polarized light differ from the conditions that determine the s-polarization resonant modes. This means that s- and p-polarized resonant modes do not occur at the same frequencies, but are shifted in frequency by an amount $\Delta v_1$.

In the apparatus of FIG. 7, $\Delta v_1 = \Delta v$. That is, modulator 20 shifts the frequency of beam 212B by an amount $\Delta v$ equal to the difference between s- and p-resonant frequencies. This enables both the s- and the p-polarized components of intracavity beam 28 to simultaneously resonate within ring resonator 231. The s- and p-resonances occur at different frequencies, but this difference is precisely compensated for by the frequency shift $\Delta v$ produces in beam 212B by modulator 220.

In the preferred embodiment, only $TEM_{00}$ modes are excited. The difference between the frequency of an s-polarized TEMoo mode and the frequency of the corresponding p-polarized $TEM_{00}$ mode is $\Delta v_1$. The frequency shift induced by modulator 220, $\Delta v$, is equal to $\Delta v_1$.

Mirror 234 is attached to a translator 236 that moves mirror 234 along a z-axis, as shown in FIG. 7. Translator 236 changes the distance between mirror 234 and mirror 230, and thereby changes the round trip distance D. Using translator 236 to move mirror 234 therefore results in changing the frequencies of the resonant modes of ring resonator 231. In the preferred embodiment, translator 236 comprises a piezo-electric transducer, and is capable of moving mirror 234 several microns.

A beam 244 extends from ring resonator 231. A component of beam 244 is a portion of beam 226 that is reflected by mirror 230. Another component of beam 244 is a portion of intracavity beam 228 that leaks through mirror 230. Beam 244 passes through a polarizer 241 that isolates light having the same polarization (either p or s) as polarization P1 of beam 212A.

The portion of beam 244 having polarization P1 is a tracking beam 244A. In the preferred embodiment, tracking beam 244A has p-polarization, and is transmitted by polarizer 241 to a detector 240. Polarizer 241 is any kind of polarizer, such as a polarizing cube beamsplitter or a Wollaston, Glan-Taylor, or Glan-Thomson prism. Detector 240 is any low noise photosensitive device such as a photovoltaic, photoconducting, photoemissive, thermopile, or pyroelectric detector. Detector 240 is preferably a silicon, GaAs, or InGaAs PIN photodiode.

Detector 240 sends an electrical output signal to a tracking circuit 250. Tracking circuit 250 band-pass filters the signal around the modulation frequency of phase modulator 222 using a mixer to multiply the signal and the modulation frequency. Tracking circuit 250 then mixes the filtered signal to DC using a low-pass filter. The result is the well known Pound-Drever error signal.

In essence, the Pound-Drever error signal gives the difference between the received intensities of sideband 272B and sideband 272A of FIG. 2. In the preferred embodiment, the sidebands are shifted in frequency from central frequency peak 270 by an amount less than the free spectral range of ring resonator 231. In this embodiment, the Pound-Drever error signal is linearly proportional to a difference between a resonant frequency of ring resonator 231 and the mean frequency of beam 212. Referring again to FIG. 7, the Pound-Drever error signal is zero when the portion of beam 226 that has polarization P1 is resonantly coupled to ring resonator 231. Since the frequency of beam 212B is shifted by modulator 220, the portion of beam 226 that has polarization P2 is also resonantly coupled to ring resonator 231 when the Pound-Drever error signal is zero.

Tracking circuit 250 is electrically connected to translator 236, and thereby moves mirror 234 in an oscillating motion around a central value corresponding to a resonant coupling between beam 226 and ring resonator 231. Preferably, tracking circuit 250 sends an oscillating voltage to translator 236 to achieve the oscillating motion. The oscillations are preferably sinusoidal, but may have saw-tooth or any other desired form.

It will be clear to one skilled in the art that the above embodiment may be altered in many ways without departing from the scope of the invention. Accordingly, the scope of the invention should be determined by the following claims and their legal equivalents.

We claim:

1. A ring-down spectroscopy system comprising:
   a) a ring resonator having at least a first mirror and a second mirror;
   b) a translator attached to said first mirror for controllably moving said first mirror;
   c) a source of continuous wave input laser light, wherein said input laser light comprises a first component having a first polarization and a second component having a second polarization;
   d) optics configured to couple said input laser light into said ring resonator;
   e) a frequency shifter, disposed in a path of said first component of said input laser light, configured to shift a mean frequency of said first component of said input laser light with respect to a mean frequency of said second component of said input laser light by a frequency shift $\Delta v$;
   f) a first detector having a first detector output, wherein said first detector is configured to measure an intensity of a signal beam exiting from said ring resonator, said signal beam having said first polarization; and
   g) a second detector having a second detector output, wherein said second detector is configured to measure an intensity of a tracking beam exiting from said ring resonator, said tracking beam having said second polarization.

2. The system of claim 1, wherein said frequency shift $\Delta v$ is equal to a difference between
   a first resonant frequency of said ring resonator corresponding to a first mode having said first polarization, and
   a second resonant frequency of said ring resonator corresponding to a second mode having said second polarization.

3. The system of claim 1, further comprising a phase modulator disposed in a path of said second component of said input laser light, said phase modulator inducing side bands in said second component of said input laser light.

4. The system of claim 1, further comprising a tracking circuit electrically connected to said second detector output and to said translator, wherein said tracking circuit is configured to:
   receive an input from said second detector output,
   use said input to determine an oscillating voltage, and
   deliver said oscillating voltage to said translator, thereby causing a position of said first mirror to oscillate around a central value corresponding to a resonant coupling between said ring resonator and said first component of said input laser light.

5. The system of claim 1, further comprising a threshold detector electrically connected to said first detector output and to said frequency shifter, wherein said threshold detector delivers a trigger pulse to said frequency shifter when said intensity of said signal beam reaches a predetermined value, said trigger pulse causing said frequency shifter to temporarily change said frequency shift $\Delta v$, thereby temporarily decoupling said first component of said input laser light from said ring resonator.

6. The system of claim 5, further comprising electronics connected to said first detector output and to said threshold detector, for gathering a ring-down wave form.

7. The system of claim 1, wherein said frequency shifter comprises an acousto-optic modulator.

8. The system of claim 1, wherein said first polarization is s-polarization and said second polarization is p-polarization.

9. The system of claim 1, wherein said source for producing said continuous wave input laser light comprises a laser.

10. The system of claim 9, wherein said laser is a diode laser.

11. The system of claim 9, wherein said laser is a tunable laser.

12. The system of claim 1, wherein said ring resonator further comprises a third mirror.

13. The system of claim 12, wherein: said optics are positioned to couple said input laser light into said ring resonator through said second mirror, and said signal beam exits through said third mirror.

14. The system of claim 12, wherein said first mirror is plano/concave, and wherein said second and third mirrors are plano/plano.

15. The system of claim 12, wherein said first, second, and third mirrors are positioned such that $TEM_{01}$ modes of said ring resonator are separated from $TEM_{10}$ and $TEM_{01}$ modes by half a free spectral range of said ring resonator.

16. The system of claim 1, wherein said translator comprises a piezo-electric transducer.

17. A ring-down spectroscopy system, comprising:
   a continuous wave light source (CWLS);
   an optical ring-down cavity optically coupled to said continuous wave light source (CWLS);
   an optical isolator, configured to isolate said continuous wave light source (CWLS) from said ring-down cavity;
   mode-matching optics disposed between said continuous wave light source (CWLS) and said ring-down cavity;
   a photodetector configured to detect radiation exiting said ring-down cavity;
   a threshold detector coupled to said photodetector;
   a cavity tracking circuit coupled to said threshold detector and said photodetector; and
   a processor unit coupled to said threshold detector, said tracking circuit and said photodetector.

18. The system of claim 17 wherein said continuous wave light source (CWLS) is a transverse mode tunable laser.

19. The system of claim 18 wherein said laser is a single frequency tunable external cavity diode laser.

20. The system of claim 18 wherein said laser is a distributed feedback (DFB) laser diode.

21. The system of claim 17 wherein said ring-down cavity is a linear Fabry-Perot resonator, having two or more mirrors.

22. The system of claim 21 wherein said mirrors are spherical.

23. The system of claim 22 wherein said mirrors have a reflectivity greater than 99.9%.

24. The system of claim 21 wherein said mirrors are to provide a triply degenerate cavity having modes split into three groups equally spaced within the free spectral interval of said ring-down cavity.

25. The system of claim 21 wherein at least one of said mirrors is translatably mounted to allow the length L of said ring-down cavity to be varied.

26. The method of claim 25 wherein a translational motion is implemented by mounting one of said mirrors to a piezo-electric transducer (PZT).

27. The system of claim 17 wherein said isolator includes an acousto-optic modulator (AOM).

28. The system of claim 27 wherein said isolator further includes a Faraday isolator.

29. The system of claim 27 wherein said acousto-optic modulator (AOM) is configured to shift an optical frequency of radiation reflected from said ring down cavity by twice the value of a driving frequency and acts as a switch to turn said radiation from said continuous wave light source (CWLS) on and off so that ring-down can be observed.

30. The system of claim 27 wherein said acousto-optic modulator (AOM) is configured to operate in a deflection mode to optically couple radiation to said ring-down cavity.

31. The system of claim 17 wherein said mode-matching optics are configured to excite single-transverse and longitudinal modes in said ring-down cavity.

32. The system of claim 17 wherein said mode-matching optics include a pinhole and at least one lens.

33. The system of claim 17, wherein said photodetector is a low noise photodetector.

34. The system of claim 33 wherein said photodetector is a Si or InGaAs PIN photodiode.

35. The system of claim 17 wherein an output signal of said photodetector is coupled to said threshold detector, which generates a trigger signal as soon as the output signal of said ring-down cavity exceeds a predefined adjustable level.

36. The system of claim 35 wherein said trigger signal controls said cavity tracking circuit.

37. The system of claim 17 wherein said processor unit includes a digitizer, a memory and a timer.

38. A ring-down spectroscopy method, comprising:
   (a) coupling radiation from a continuous-wave light source (CWLS) into a ring-down cavity such that during sweeping a frequency of said radiation by one or more free spectral ranges of said ring-down cavity one or more resonant modes of the cavity are excited;
   (b) modulating said radiation by less than one free spectral range of said ring-down cavity;
   (c) triggering a threshold detector when a fundamental mode of said ring-down cavity reaches a predetermined threshold value;
   (d) producing a trigger signal with said threshold detector to trigger a digitizer to sample a ring-down decay curve;
   (e) generating a plurality of waveform points from said ring-down decay curve and stored said waveform points in a memory of a processor;
   (f) extrapolating a decay constant from a logarithm of said waveform points; and
   (g) determining a point on an absorption spectrum from said decay constant.

39. The method of claim 38 further comprising tuning said continuous-wave light source (CWLS) over a frequency or wavelength range and repeating steps (a)–(g) to determine a portion of said absorption spectrum.

40. The method of claim 39 wherein said fundamental mode is a $TEM_{00}$ mode.

41. The method of claim 40 wherein said one or more resonant modes further includes a $TEM_{00}$ cavity mode and a $TEM_{02}$ cavity mode.

42. The method of claim 38 further comprising aligning mode matching optics disposed between said continuous wave light source (CWLS) and said ring-down cavity such that the excitation efficiency of one or more higher modes of said ring-down cavity is reduced by a factor of between about 20 to 100, compared to said fundamental cavity mode.

43. The method of claim 38 wherein a configuration of said ring-down cavity is close to that of a degenerate case.

44. The method of claim 43 wherein said ring-down cavity has a triply degenerate cavity configuration.

45. A ring-down spectroscopy method comprising the following steps:
   a) producing continuous wave input light comprising a first component having a first polarization and a second component having a second polarization;
   b) shifting a mean frequency of said first component of said input light with respect to a mean frequency of said second component of said input light by a frequency shift $\Delta v$;

c) coupling said first and second components of said input light into a ring resonator comprising first and second mirrors;

d) moving said first mirror in a vicinity of a fiducial position corresponding to resonant coupling between said first component of said input light and said ring resonator;

e) detecting an intensity of a signal beam exiting from said ring resonator, said signal beam having said first polarization; and f) detecting an intensity of a tracking beam exiting from said ring resonator, said tracking beam having said second polarization.

46. The method of claim 45, wherein said step of moving said first mirror comprises a step of oscillating said mirror about said fiducial position.

47. The method of claim 45, wherein said step of moving said first mirror comprises a step of scanning said first mirror over a distance corresponding to a free spectral range of said ring resonator.

48. The method of claim 45, wherein said step of moving said first mirror comprises a step of scanning said first mirror in one direction until said signal beam reaches a threshold intensity.

49. The method of claim 45, further comprising the steps of:

a) temporarily altering said frequency shift $\Delta v$ when said signal beam reaches a threshold intensity, thereby temporarily decoupling said first component of said input light from said ring resonator, and b) recording said intensity of said signal beam as a function of time, thereby obtaining a ring-down wave form.

50. The method of claim 45, further comprising the step of scanning said mean frequencies of said first and second components of said input light, thereby changing said fiducial position.

51. The method of claim 45, further comprising the steps of:

a) inducing side bands on said second component of said input light;

b) using said intensity of said tracking light to generate an error signal;

c) using said error signal to generate an offset voltage and an amplitude of an oscillating voltage; and wherein said step of moving said first mirror comprises a step of using said voltages to oscillate said mirror about said fiducial position.

52. The method of claim 45, wherein said frequency shift $\Delta v$ is equal to a difference between a first resonant frequency of said ring resonator corresponding to a first mode having said first polarization, and a second resonant frequency of said ring resonator corresponding to a second mode having said second polarization.

53. The method of claim 45, wherein said first polarization is s-polarization and said second polarization is p-polarization.

* * * * *